United States Patent [19]

Mulvey et al.

[11] 4,145,364

[45] Mar. 20, 1979

[54] PREPARATION OF FLUORINATED ANILINES

[75] Inventors: Dennis M. Mulvey, Milford; Leonard M. Weinstock, Bellemead, both of N.J.

[73] Assignee: Merck & Co., Inc., Rahway, N.J.

[21] Appl. No.: 855,649

[22] Filed: Nov. 30, 1977

[51] Int. Cl.² ............................................. C07C 85/11
[52] U.S. Cl. ................................ 260/578; 260/465 D; 260/465 E; 260/575; 560/18; 560/19; 560/22; 560/46; 560/47; 560/142
[58] Field of Search ................... 260/578, 575, 465 E; 560/47, 46, 19, 22

[56] References Cited

PUBLICATIONS

Bamberger, "Ann.", 424, pp. 233–263 (1921).
Heller et al., "Nature", 168, pp. 909–910 (1951).
Patrick et al., "J. Org. Chem.", 39(12), pp. 1758–1761 (1974).
Bachrach et al., "Organic Synthesis", IV, pp. 74–78 (1954).
Finger et al., "J. Am. Chem. Soc.", 78, pp. 6034–6037 (1956).

*Primary Examiner*—Winston A. Douglas
*Assistant Examiner*—John Doll
*Attorney, Agent, or Firm*—Raymond M. Speer; Mario A. Monaco

[57] ABSTRACT

Fluorinated anilines, especially p-fluoroaniline and 2,4-difluoroaniline, are prepared by treating aromatic azides with anhydrous hydrogen fluoride. The aromatic azides, in turn, are prepared from the corresponding anilines by treatment with nitrous acid or salt thereof and an alkali metal azide in the presence of a mineral acid, and in an aqueous-nonaqueous, two-phase environment.

23 Claims, No Drawings

PREPARATION OF FLUORINATED ANILINES

BACKGROUND OF THE INVENTION (1) Field of the Invention

The present invention is concerned with a novel improved method for preparing fluorinated anilines, especially 2,4-difluoroaniline, which comprises treating aromatic azides with anhydrous hydrogen fluoride.

The fluorinated anilines and substituted fluorinated anilines with whose preparation the present invention is concerned are largely known compounds possessing a variety of utilities. For example, p-fluoroaniline is a known compound of known utility described in U.S. Pat. No. 2,884,458. In addition, p-fluoroaniline and substituted p-fluoroanilines are useful starting materials for preparation of the substituted 5-(phenyl) benzoic acid anti-inflammatory compounds described in U.S. Pat. Nos. 3,681,445 and 3,692,821.

The present invention is especially concerned with preparation of 2,4-difluoroaniline, which is a well known starting material and intermediate for a number of organic syntheses. See The Merck Index, ninth edition, pg. 415 (1976). Particularly, 2,4-difluoroaniline and substituted derivatives thereof prepared by the method of the present invention are useful as starting materials for preparation of 2',4'-difluoro-4-4-hydroxy-[1,1'-biphenyl] -3-carboxylic acid, and derivatives thereof, which are valuable anti-inflammatory and analgesic agents for therapeutic use. See U.S. Pat. No. 3,714,226.

(2) Description of the Prior Art

The method of the present invention for preparing fluorinated anilines, in contrast to the prior art, provides reaction conditions which are mild, achieves complete selectivity, and tolerates a wide variety of functionality in the reactants. Heretofore, methods for the selective introduction of fluorine into unsubstituted positions of aromatic species have been scarce, in contrast to other halogenation techniques. Direct fluorination has usually involved the use of highly reactive species which have suffered from a corresponding inconvenience of handling. Thus, the following materials have been employed: elemental fluorine: Sheppard and Sharts, "Organic Fluorine Chemistry", W. A. Benjamin, New York, N.Y., 1969; inert gas fluorides: Shaw et al., J. Am. Chem. Soc., 92, 6498 (1970); and high valent metal fluorides: Sheppard and Sharts, op. cit.

Two methods which have been employed for introducing fluorine selectively have required that the introduction be at the site of an existent functionality. These two methods are the Balz-Schiemann reaction, described by Suschitsky, Adv. Fluorine Chem., 4, 1 (1965), and the metathesis of activated aromatic halides, described by Finger and Kruse, J. Am. Chem. Soc., 78, 6043 (1956). Also, there has recently been reported a method involving thallation of selected aromatic species followed by fluorine introduction. See, Taylor et al., J. Org. Chem., 42 (2), 362 (1977).

There have also been employed in the past, methods involving the reaction of arylhydroxylamines with anhydrous hydrogen fluoride, which have given moderate yields of p-fluoroanilines. See Titov and Baryshnikova, Zhur. Obshchei. Khim., 23, 346 (1953), and Patrick et al., J. Org. Chem., 39 (12), 1758 (1974). These methods involve essentially a Bamberger rearrangement of the type described in Bamberger, Ann., 424, 233 (1921), which involved other (not HF) hydrogen halides. However, while Bamberger reported both ortho and para attack with the other hydrogen halides employed, in the method of the present invention it has been found that hydrogen fluoride results only in para attack of the starting material.

It has also been suggested that the Bamberger rearrangement proceeds by way of a nitrenium ion whether arylhydroxylamine or arylazide serves as the precursor. See Ingold et al., Nature, 168, 909 (1951). However, the arylazide route of the present invention, in contrast to the arylhydroxylamine route, provides clean monofluorinated products in good yield with tolerance of functional groups and steric considerations not being critical. The arylhydroxylamine route suffers from the disadvantage of concomitant formation of corresponding unfluorinated aniline, as well as the symmetrical azo and azoxy compounds. Further, considerable tar is formed, making product isolation difficult. Product separation is further complicated by the nearness of the boiling points of the fluorinated and non-fluorinated anilines.

U.S. Pat. Nos. 2,198,249; 2,884,458; 3,558,707 and 3,639,482 describe preparation of p-fluoroaniline by catalytic hydrogenation of the corresponding nitrobenzene. U.S. Pat. No. 3,900,519 describes preparation of p-fluoroaniline from the corresponding p-halonitrobenzenes by reaction with anhydrous hydrogen fluoride in the presence of a deoxygenating agent. None of the disclosures of these patents suggests, however, the preparation method of the present invention.

SUMMARY OF THE INVENTION

In accordance with the method of the present invention there are prepared fluorinated anilines of structural formula:

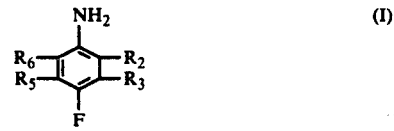

where $R_2$, $R_3$, $R_5$, and $R_6$ may be the same or different and are independently selected from hydrogen; $C_{1-6}$ alkyl, for example, methyl, ethyl and t-butyl; $C_{1-6}$ alkenyl, for example, allyl and propenyl; halo, for example, bromo, chloro, and fluoro; halo $C_{1-4}$ alkyl, for example, chloromethyl and trifluoromethyl; $C_{1-6}$ alkoxy, for example, methoxy, ethoxy and butoxy; $C_{1-4}$ alkoxycarbonyl, for example, carbomethoxy; acyloxy, for example, acetyloxy; acyl, for example, propionyl and benzoyl; $C_{1-4}$ alkylthio, for example, methylthio; hydroxy $C_{1-4}$ alkyl, for example, hydroxyethyl; hydroxy; amino; cyano; and nitro.

The fluorinated anilines described above are prepared by reacting an azide compound of structural formula:

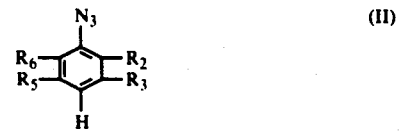

where $R_2$, $R_3$, $R_5$, and $R_6$ have the same meaning as above, with hydrogen fluoride under essentially anhydrous conditions.

Thus, the method of the present invention may be schematically represented as follows:

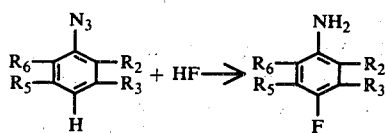

As already discussed above, the method of the present invention offers the advantages of clean final product, good yields, and tolerance of the various substituents $R_2$, $R_3$, $R_5$ and $R_6$.

Illustrative of the various starting materials of Formula II which may be employed in the method of the present invention are the following:

phenylazide
2-methyl-5-chlorophenylazide
2,6-diethyl-3-bromophenylazide
2,6-dimethylphenylazide
3,5-dimethylphenylazide
2,5-dimethoxyphenylazide
2-trifluoromethylphenylazide
2-chlorophenylazide
2-fluorophenylazide
3-butoxy-6-propenylphenylazide
3,5-dicarbethoxyphenylazide
5-acetyloxyphenylazide
3-propionyl-6-chloroethylphenylazide
3-benzoylphenylazide
3-cyanophenylazide
3-acetylphenylazide
3-methoxyphenylazide
5-cyanophenylazide
3-nitro-5-methylphenylazide The method of the present invention must be carried out under essentially anhydrous conditions. That is, traces of water can be tolerated, but water adversely affects the course of the reaction and so efforts are made to achieve anhydrous conditions. Consequently, an anhydrous organic solvent medium for the reaction is chosen. The solvent is selected from $C_{1-18}$ alkane, for example, n-hexane, iso-octane, and n-dodecane; halo $C_{1-18}$ alkane, for example, dichloromethane, dichloroethane, and fluorohexane; and cyclo $C_{1-10}$ alkane, for example, cyclopentane, cyclohexane and cyclononane. However, aromatic hydrocarbon solvents such as benzene, alcohol and ether solvents, and water, are not useful as the organic solvent medium in which the reaction is carried out. The amount of organic solvent medium employed may be varied from about 3 parts to about 20 parts by weight of solvent to 1 part by weight of azide compound starting material. Preferably, from about 5 parts to about 15 parts, and most preferably about 10 parts by weight of solvent to 1 part by weight of azide compound starting material are employed.

In carrying out the method of the present invention, anhydrous hydrogen fluoride is employed in a molar ratio to the azide compound starting material of at least 1:1. It is desirable to employ a slight excess of the anhydrous hydrogen fluoride. Lesser amounts will detrimentally affect yield. Thus, the molar ratio of anhydrous hydrogen fluoride to azide compound starting material may be from 1:1 to 10:1 and is preferably from 1:1 to 2:1.

The method of the present invention may be carried out at temperatures of from about $-80°$ C. to about $50°$ C., preferably from about $-10°$ C. to about $10°$ C. The reaction is suitably carried out at ambient pressures, although external pressures of the order of up to 1200 psia may be applied to the reaction environment.

The time period over which the method of the present invention may be carried out may be varied considerably, from about 1 hour to about 24 hours. Preferably, however, the reaction is carried out over a period of from about 1 hour to about 10 hours.

After the reaction has been carried to completion to produce the desired fluorinated aniline, the desired final product can be readily separated from the reaction mixture by conventional means such as simple extraction, distillation, or fractional crystallization. These techniques may also be employed to further purify the separated final product.

The present invention is particularly concerned with preparation of 2,4-difluoroaniline. Accordingly, the azide compound starting material for the reaction will be 2-fluorophenylazide.

In the method of the present invention it is also possible to employ bis-azide compound starting materials. In this way it is possible to produce a 2,4-difluoroaniline directly without employing a fluorine-substituted azide compound starting material. Thus, meta-phenylbisazide is reacted with anhydrous hydrogen fluoride to produce 2,4-difluoro-5-aminoaniline.

In addition to the reaction of an azide compound starting material with anhydrous hydrogen fluoride to produce fluorinated anilines as described above, the present invention is also concerned with a two step method in which aniline or a substituted aniline of structural formula:

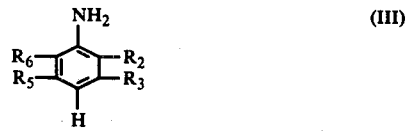

where $R_2$, $R_3$, $R_5$, and $R_6$ have the same meaning as above, is reacted with nitrous acid or salt thereof, preferably an alkali metal or alkaline earth metal salt thereof, and an alkali metal azide, preferably sodium azide, $NaN_3$, to produce the corresponding azide; and this azide compound is, in turn, reacted with anhydrous hydrogen fluoride to produce the desired fluorinated aniline, as has been discussed in detail above.

The first step of preparing the azide compound from the corresponding aniline is carried out in the presence of a mineral acid, preferably hydrochloric acid. The total reaction sequence may be illustrated as follows:

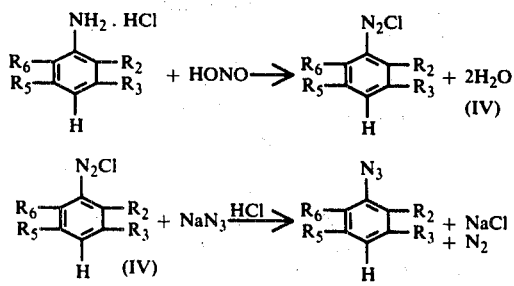

where $R_2$, $R_3$, $R_5$ and $R_6$ have the same meaning as above. A general description of the above reaction may be found in *Organic Syntheses*, Coll. Vol. IV, pp. 74–78.

In a typical procedure for carrying out the first step of preparing the azide compound, as outlined above, a cold, two-phase mixture of the aryl diazonium salt (Formula IV) in water and n-hexane, which has been generated in situ from the aniline starting material with hydrochloric acid and nitrous acid, is treated with a solution of sodium azide in water. Although it would be possible to eliminate the solvent altogether and allow the azide compound to separate out, usually as an oil, such a procedure would isolate the hazardous azide compound. By employing a solvent in which the azide compound is taken up, the hazard of isolation is avoided. Further, the solvent employed is that which is necessary for the succeeding step of preparing the fluorinated aniline, thus permitting a through process in which the two steps are carried out essentially as one step without isolation of the azide compound intermediate. Thus, as the azide is formed it is extracted into the hexane layer, which after about two hours is separated and charged to a vessel containing excess anhydrous hydrogen fluoride for the second step of preparing the fluorinated aniline. After about four hours, the reaction is quenched, rendered alkaline, and the fluoroaniline final product is isolated by extraction. It can be seen that the above method of two steps in one which can be carried out as a through process in which the potentially hazardous azides need not be isolated. Thus, the reactions of the two steps of this method of the present invention may be illustrated as follows:

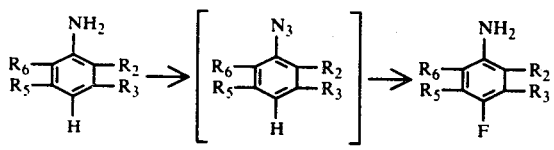

where $R_2$, $R_3$, $R_5$, and $R_6$ have the same meaning as above.

The first step of azide compound preparation is carried out in a two phase environment in which one phase is aqueous and contains the aryl diazonium salt and sodium azide, and the other, nonaqueous, phase is an organic solvent selected from $C_{1-18}$ alkane, for example, n-hexane; halo $C_{1-18}$ alkane, for example, dichloroethane; and cyclo $C_{1-10}$ alkane, for example, cyclohexane. The amount of organic solvent employed may be varied from about 2 parts to about 25 parts by weight of solvent to 1 part by weight of aniline compound starting material. The weight ratio of organic solvent to water for the two phase environment should be from about 1:2 to about 2:1.

The first step of azide compound preparation may be carried out at temperatures of from about −5° C. to about 25° C. preferably from about −2° C. to about 10° C. Since an aqueous phase is present, use of temperatures too far below 0° C. will not be possible. The time period over which the first step may be carried out will vary from about 1 hour to about 10 hours, but will usually be complete in from about 2 hours to about 4 hours time.

After the reaction has been carried to completion and the desired azide compound is produced, the second step of fluorinated aniline preparation is carried out without separation of the azide compound, as has already been described. This is accomplished simply by separating the organic solvent phase of the two phase environment for the first step of the method. The organic solvent will have extracted the azide compound as it was formed during the first step of the method. The second step of fluorinated aniline compound preparation then proceeds using the azide compound prepared during the first step, contained in the organic solvent. This second step is carried out in accordance with the procedures and parameters described earlier for preparation of the fluorinated anilines from the azide compound starting materials.

The present invention is particularly concerned with preparation of 2,4-difluoroaniline. Accordingly, there is provided not only a method for preparing the azide compound starting material in accordance with the procedures described above, but also a method of preparing the aniline starting material as well. Thus, the total method, which employs the readily available and inexpensive starting material 2-chloronitrobenzene, comprises the following sequence of steps: (a) reacting 2-chloronitrobenzene with potassium fluoride to form 2-fluoronitrobenzene; (b) hydrogenating the 2-fluoronitrobenzene to form 2-fluoroaniline; (c) reacting the 2-fluoroaniline with an alkali metal azide in the presence of a mineral acid and nitrous acid or a salt thereof to form 2-fluorophenylazide; and (d) reacting the 2-fluorophenylazide with hydrogen fluoride under essentially anhydrous conditions. The above series of steps may be illustrated as follows:

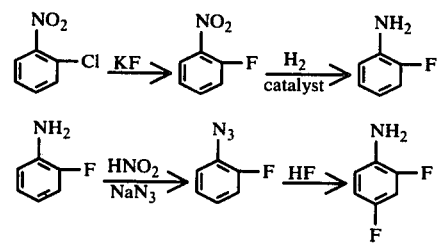

The method of the present invention will be better understood from the following illustrative examples which provide a detailed explanation of the manner in which the method of the present invention may be carried out.

EXAMPLE 1

Preparation of 4-fluoroaniline

A solution of 5g. of phenylazide in 20g. of n-hexane was charged to a bomb together with 40 ml. of anhydrous hydrogen fluoride and shaken for 24 hours at room temperature. The reaction mixture was then vented, blown down with nitrogen, and removed from the bomb with the aid of 100 ml. of water. The reaction mixture was then cooled, made basic with KOH, and extracted three times with ether, using 100 ml. per extraction. A mechanical loss of about 40% of the material was experienced. The reaction product was dried over $MgSO_4$ to yield 2.4g. (52%) of final product. The 4-fluoroaniline structure of the final product was confirmed by IR and NMR. The product had a b.p. of 88°–90° C. at 40 mm. Hg.

EXAMPLE 2

Preparation of 2,4-difluoroaniline

Step A: Preparation of 2-fluorophenylazide

A mixture of 4.44g. (0.04 mole) of 2-fluoroaniline in 16 ml. of water and 9 ml. of concentrated HCl, kept at 0°–5° C., was treated with a solution of 2.90g. (0.04 mole) of $NaNO_2$ in 10 ml. of water. The reaction mixture was aged for one-half hour at 0°–5° C. and there was then added slowly to the mixture a solution of 2.6g. (0.04 mole) of $NaN_3$ in 10 ml. of water. The reaction mixture was then allowed to slowly reach room temperature, and it was noted that a gas was evolved. There was then added 40 ml. of petroleum ether, and the reaction mixture was shaken well, after which it was observed to separate into two separate layers. The yellow petroleum ether layer was separated, dried over $MgSO_4$, and concentrated under reduced pressure at a temperature of about 30° C. There was produced 5.5g. of a yellow oil and the structure of the final product was confirmed by IR.

Step B: Preparation of 2,4-difluoroaniline

A solution of 4.11g. (0.03 mole) of 2-fluorophenylazide in 81 ml. of cyclohexane was treated with 20 ml. of hydrogen fluoride. The reaction mixture was then shaken at room temperature for 24 hours, then cooled, vented, and rinsed from the bomb with two successive applications of 100 ml. of dichloromethane and then 100 ml. of water. The reaction mixture was then blown down under nitrogen, quenched in 75g. of ice, and rendered basic with KOH pellets. The reaction mixture was extracted with dichloromethane to yield 2.2g. (57%) of a brown-red fluid after drying over $MgSO_4$. The 2,4-difluoroaniline structure of the final product was confirmed by IR, and the product had a b.p. of 90°–92° C. at 40 mm. Hg.

EXAMPLE 3

Preparation of 2-trifluoromethyl-4-fluoroaniline

Step A: Preparation of 2-trifluoromethylphenylazide

A solution of 12.88g. (0.08 mole) of 2-trifluoroaniline in 32 ml. of water and 18 ml. of concentrated HCl was cooled to 0° C. A clear to tan solution was obtained. Then, a solution of 6.07g. (0.088 mole) of $NaNO_2$ in 20 ml. of water was added dropwise to the solution and a yellow precipitate was observed to form. The reaction mixture was aged 20 minutes at 0°–5° C., after which 5.72g. (0.088 mole) $NaN_3$ in 20 ml. of water, and 100 ml. of n-hexane were added slowly, allowing for degassing of the reaction mixture between additions. A yellow color was observed to form in the hexane layer. The reaction mixture was aged for one-half hour, after which the hexane layer was separated, dried over $MgSO_4$, and concentrated under reduced pressure to yield 13.58g. (91%) of a yellow solid. Structure of the product was confirmed by IR.

Step B: Preparation of 2-trifluoromethyl-4-fluoroaniline

A mixture of 13.58g. (0.07 mole) of 2-trifluoromethylphenylazide, 100 ml. of hexane, and 20 ml. of anhydrous hydrogen fluoride was treated with 1.0g. of $AlF_3$, and the reaction mixture was then aged for 10 hours at room temperature with agitation. The reaction mixture was then cooled, vented, and rinsed from the bomb with 60 ml. of dichloromethane, followed by 50 ml. of water. After blowing off the hydrogen fluoride, the aqueous rinse was added to the residue, which was cooled to 0° C. and made alkaline (pH about 11) with KOH pellets. The residue was then extracted twice with 100 ml. of dichloromethane per extraction; and the extracts were dried over $MgSO_4$, and then concentrated under reduced pressure to yield 9.68g. (77%) of a brown oil. Structure of the final product as 2-trifluoromethyl-4-fluoroaniline was confirmed by IR and NMR. The final product had a b.p. of 87°–90° C. at 40 mm. Hg.

EXAMPLE 4

Preparation of 3,5-dimethyl-4-fluoroaniline

Step A: Preparation of 3,5-dimethylphenylazide

A solution of 9.68g. (0.08 mole) of 3,5-dimethylaniline in 100 ml. of water and 10 ml. of concentrated HCl was cooled to 0° C. Then a solution of 6.07g. (0.088 mole) of $NaNO_2$ in 20 ml. of water was added dropwise to the solution of 3,5-dimethylaniline, and the reaction mixture was aged for one-half hour. There was then added to the reaction mixture 70 ml. of n-hexane followed by a solution of 5.72g. (0.088 mole) of $NaN_3$ in 20 ml. of water which was added dropwise and accompanied by vigorous evolution of gas from the reaction mixture. The reaction mixture was then stirred for 15 minutes at room temperature. Separate layers were observed to form and the hexane layer was noted to have a deep yellow color. The reaction mixture was extracted again with 50 ml. of hexane, and the combined hexane extracts were dried over $MgSO_4$ and concentrated to a volume of 95 ml. Structure of the final product was confirmed by IR. The 95 ml. solution of product was used as a starting material for Step B below.

Step B: Preparation of 3,5-dimethyl-4-fluoroaniline

The 95 ml. hexane solution of 3,5-dimethylphenylazide prepared in Step A above was charged to a rocker bomb and 20 ml. of hydrogen fluoride was added. The reaction mixture was then aged for 10 hours at room temperature with agitation, after which it was cooled, vented, and poured from the bomb, and the bomb rinsed with 40 ml. of water and 40 ml. of dichloromethane. The combined hexane, dichloromethane and hydrogen fluoride were blown down under nitrogen. The resulting residue was combined with the aqueous rinse, cooled to 0° C., and rendered alkaline with KOH pellets. The residue was then extracted three times with 75 ml. of dichloromethane per extraction, and the combined extracts dried over $MgSO_4$ and then concentrated under reduced pressure to yield 7.34g. (66.2%) of a brown-red oil. This oil was then vacuum distilled at 40 mm. Hg to give 6.70g. of a colorless oil, a 60% yield. The final product had a b.p. of 127°–130° C. at 40 mm. Hg.

EXAMPLE 5

Preparation of 2,4-difluoroaniline

A solution of 15.7g. (0.1 mole) of o-chloronitrobenzene in 150 ml. of tetramethylsulfone was treated with 11.6g. (0.2 mole) of potassium fluoride, and the mixture heated at 195° C. for 10 hours with stirring. After cooling to room temperature, the reaction mixture was diluted with 250 ml. of dichloromethane and 200 ml. of water. The resulting layers were separated and the dichloromethane layer was treated with 0.5g. of 10% palladium carbon catalyst. After shaking with hydrogen until uptake ceased (about 3 hours at 45 psig), the reaction mixture was filtered to recover the catalyst. The reaction mixture filtrate was extracted four times with 100 ml. of 2.5 N HCl per extraction, and the organic layer was separated and saved for tetramethylsulfone recovery. The aqueous acid layer was cooled and carried on into the succeeding steps, which were the same as those described in Example 2, Steps A and B above.

EXAMPLE 6

Preparation of 3-cyano-4-fluoroaniline

Step A: Preparation of 3-cyanophenylazide

A suspension of 9.44g. (0.08 mole) of 3-cyanoaniline in 50 ml. of water at 0° C. was treated with 20 ml. of concentrated HCl, with slow addition, maintaining the reaction mixture temperature at or below 5° C. There was then added a solution of 6.07g. (0.088 mole) of $NaNO_2$ in 20 ml. of water, and the reaction mixture was aged for ½ hour at 0°-5° C. Then to the clear reaction mixture solution was added 75 ml. of hexane, followed by a solution of 5.72g. (0.088 mole) of $NaN_3$ in 20 ml. of water, which were added dropwise with stirring. A precipitate was observed to form, after which 100 ml. of ether was added. The organic and aqueous components of the reaction mixture was separated and the aqueous component was extracted with 100 ml. of ether. The organic component was dried over $MgSO_4$ and concentrated to a volume of about 100 ml. An aliquot was blown down and the structure of the product confirmed for 3-cyanophenylazide.

Step B: Preparation of 3-cyano-4-fluoroaniline

A 50 ml. ether and hexane solution of 9.8g. of 3-cyanophenylazide prepared in Step A above was charged to a rocker bomb and the ether and hexane were blown down under nitrogen. Then, 100 ml. of hexane was introduced, followed by 20 ml. of concentrated hydrogen fluoride, after which the bomb was shaken at room temperature for 10 hours. The reaction mixture was cooled, vented, and poured from the bomb, and the bomb rinsed with 40 ml. of water and 40 ml. of dichloromethane. The combined hexane, dichloromethane, and hydrogen fluoride were blown down under nitrogen. The resulting residue was combined with the aqueous rinse, cooled to 0° C., and rendered alkaline with $KHCO_3$. The residue was then extracted three times with 75 ml. of dichloromethane per extraction, and the combined extracts dried over $MgSO_4$ and then concentrated under reduced pressure to yield 6.5g. of a brown solid. This product was then recrystallized from boiling cyclohexane to yield 5.8g. (53%) of product with a m.p. of 88°-89° C. whose structure was confirmed by IR.

EXAMPLE 7

Preparation of 3-methoxy-4-fluoroaniline

Step A: Preparation of 3-methoxyphenylazide

A solution of 9.26g. (0.08 mole) of 3-methoxyaniline in 40 ml. of water and 20 ml. of concentrated HCl was cooled to 0° C. There was then added a solution of 6.07g. (0.088 mole) of $NaNO_2$ in 20 ml. of water, and the reaction mixture was aged for ½ hour. There was next added 70 ml. of hexane followed by dropwise addition of a solution of 5.72g. (0.088 mole) of $NaN_3$ in 20 ml. of water. After addition was complete, the reaction mixture was aged for 2 hours at room temperature. The aqueous and organic components were separated and the aqueous component was extracted with 50 ml. of hexane. The hexane component and extract were dried over $MgSO_4$ and concentrated under reduced pressure to 10.77g. (50.5%) of a yellow oil. Structure of the product as 3-methoxyphenylazide was confirmed by IR.

Step B: Preparation of 3-methoxy-4-fluoroaniline

A solution of 10.73g. (0.07 mole) of 3-methoxyphenylazide in 100 ml. of hexane was added to 20 ml. of concentrated hydrofluoric acid and the reaction mixture, contained in a bomb, was aged for 10 hours at room temperature with agitation. The reaction mixture was then cooled, vented, and poured from the bomb. The bomb was then rinsed with 50 ml. of water, followed by 20 ml. of dichloromethane. The reaction mixture poured from the bomb was blown down under nitrogen, and then combined with the bomb rinsings, and this mixture was cooled and brought to a pH of about 12 with KOH pellets. The mixture was extracted three times with 50 ml. of dichloromethane per extraction, and the combined extracts were dried over $MgSO_4$ and concentrated to 7.31g. (53%) of a dark oil. An aliquot of this product was distilled under reduced pressure to obtain a pale yellow oil with a b.p. of 150°-152° C. at 50 mm. Hg. Structure of the final product as 3-methoxy-4-fluoroaniline was confirmed by mass spectroscopy.

EXAMPLE 8

Preparation of 3-acetyl-4-flouroaniline

Step A: Preparation of 3-acetylphenylazide

A mixture of 10.8g. (0.08 mole) of 3-acetylaniline in 50 ml. of water was treated with 20 ml. of concentrated HCl and cooled to 0° C. There was then added a solution of 6.07g. (0.088 mole) of $NaNO_2$ in 20 ml. of water. The reaction mixture was aged for 20 minutes, and there was then added 25 ml. of hexane and 25 ml. of ether, followed by a solution fo 5.72g. (0.088 mole) of $NaN_3$ in 20 ml. of water. The reaction mixture was aged for ½ hour at room temperature, after which the aqueous and organic components were separated, and the aqueous component extracted with 50 ml. of ether. The organic component and extract were dried over $MgSO_4$ and concentrated under reduced pressure to 12.72g. (99%) of product whose structure as 3-acetylphenylazide was confirmed by IR.

Step B: Preparation of 3-acetyl-4-fluoroaniline

A 50 ml. ether solution of the 12.72g. of 3-acetylphenylazide prepared in Step A above was charged to a bomb and blown down under nitrogen. There was then charged to the bomb 100 ml. of hexane, 3g. of $ALF_3$, and 20 ml. of concentrated hydrofluoric acid. The reaction mixture was agitated for 10 hours and then vented and poured from the bomb. The bomb was then rinsed with 100 ml. of dichloromethane and 100 ml. of water. The reaction mixture poured from the bomb was blown down under nitrogen and mixed with the rinsings from the bomb. This mixture was then rendered alkaline while cold with KOH pellets and extracted three times with 100 ml. of dichloromethane per extraction. The combined extracts were dried over $MgSO_4$ and evaporation of the dichloromethane left 9.9g. (82%) of an orange, crystalline solid. This product was recrystallized from cyclohexane to give 8.5g. (70%) of product having a m.p. of 68°-70° C. Structure of the product as 3-acetyl-4-fluoroaniline was confirmed by IR and NMR.

What is claimed is:

1. A method of preparing fluorinated anilines of structural formula:

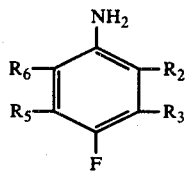

where $R_2$, $R_3$, $R_5$, and $R_6$ may be the same or different and are independently selected from hydrogen, $C_{1-6}$ alkyl, $C_{1-16}$ alkenyl, halo, halo $C_{1-4}$ alkyl, $C_{1-6}$ alkoxy, $C_{1-4}$ alkoxycarbonyl, acyloxy, acyl, $C_{1-4}$ alkylthio, hydroxy $C_{1-4}$ alkyl, hydroxy, amino, cyano, and nitro;

comprising reacting an azide compound of structural formula:

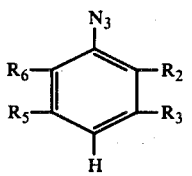

where $R_2$, $R_3$, $R_5$, and $R_6$ have the same meaning as above, with hydrogen fluoride under essentially anhydrous conditions.

2. The method of claim 1 wherein the essentially anhydrous conditions comprise an organic solvent medium wherein the solvent is selected from $C_{1-18}$ alkane, halo $C_{1-18}$ alkane, and cyclo $C_{1-10}$ alkane.

3. The method of claim 1 wherein the reaction is carried out at a temperature of from about 80° C. to about 50° C.

4. The method of claim 1 wherein the reaction is carried out over a time period of from about 1 hour to about 24 hours.

5. The method of claim 1 wherein the molar ratio of hydrogen fluoride to azide compound starting material is at least 1:1.

6. A method of preparing 2,4-difluoroaniline, comprising reacting 2-fluorophenylazide with hydrogen fluoride under essentially anhydrous conditions.

7. The method of claim 6 wherein the essentially anhydrous conditions comprise an organic solvent medium wherein the solvent is selected from $C_{1-18}$ alkane, halo $C_{1-18}$ alkane, and cyclo $C_{1-10}$ alkane.

8. The method of claim 6 wherein the reaction is carried out at a temperature of from about −80° C. to about 50° C.

9. The method of claim 6 wherein the reaction is carried out over a time period of from about 1 hour to about 24 hours.

10. The method of claim 6 wherein the molar ratio of hydrogen fluoride to 2-fluorophenylazide is at least 1:1.

11. A method of preparing fluorinated anilines of structural formula:

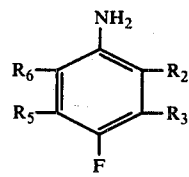

where $R_2$, $R_3$, $R_5$ and $R_6$ may be the same or different and are independently selected from hydrogen, $C_{1-6}$ alkyl, $C_{1-6}$ alkenyl, halo, halo $C_{1-4}$ alkyl, $C_{1-6}$ alkoxy, $C_{1-4}$ alkoxycarbonyl, acyloxy, acyl, $C_{1-4}$ alkylthio, hydroxy $C_{1-4}$ alkyl, hydroxy, amino, cyano, and nitro; comprising (a) reacting an aniline compound of structural formula:

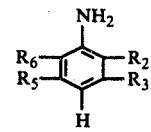

where $R_2$, $R_3$, $R_5$ and $R_6$ have the same meaning as above, with nitrous acid or alkali metal or alkaline earth metal salt thereof, and an alkali metal azide, in the presence of a mineral acid, in an aqueous-nonaqueous two-phase environment, to produce the corresponding azide compound of structural formula:

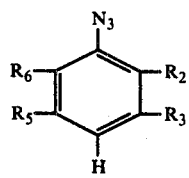

where $R_2$, $R_3$, $R_5$ and $R_6$ have the same meaning as above; and (b) reacting said corresponding azide compound with hydrogen fluoride under essentially anhydrous conditions.

12. The method of claim 11 wherein steps (a) and (b) are carried out as a through process without isolation of the corresponding azide compound intermediate product.

13. The method of claim 11 wherein sodium azide is employed.

14. The method of claim 11 wherein the mineral acid is hydrochloric acid.

15. The method of claim 11 wherein the nonaqueous phase comprises an organic solvent selected from $C_{1-18}$ alkane, halo $C_{1-18}$ alkane, and cyclo $C_{1-10}$ alkane.

16. The method of claim 11 wherein step (a) is carried out at a temperature of from about −5° C. to about 25° C.

17. The method of claim 11 wherein step (a) is carried out over a time period of from about 1 hour to about 10 hours.

18. The method of claim 11 wherein for step (a) the weight ratio of nonaqueous phase to aqueous phase is from about 1:2 to about 2:1.

19. The method of claim 11 wherein for step (b) the essentially anhydrous conditions comprise an organic solvent medium wherein the solvent is selected from $C_{1-18}$ alkane, halo $C_{1-18}$ alkane, and cyclo $C_{1-10}$ alkane.

20. The method of claim 11 wherein step (b) is carried out at a temperature of from about $-80°$ C. to about 50° C.

21. The method of claim 11 wherein step (b) is carried out over a time period of from about 1 hour to about 24 hours.

22. The method of claim 11 wherein for step (b) the molar ratio of hydrogen fluoride to azide compound starting material is at least 1:1.

23. A method of preparing 2,4-difluoroaniline comprising the steps of
(a) reacting 2-chloronitrobenzene with potassium fluoride to form 2-fluoronitro-benzene;
(b) hydrogenating the 2-fluoronitrobenzene to form 2-fluoroaniline;
(c) reacting the 2-fluoroaniline with an alkali metal azide in the presence of a mineral acid and nitrous acid or salt thereof to form 2-fluorophenylazide; and
(d) reacting the 2-fluorophenylazide with hydrogen fluoride under essentially anhydrous conditions.

* * * * *